US010457640B2

(12) United States Patent
Vaswani et al.

(10) Patent No.: US 10,457,640 B2
(45) Date of Patent: Oct. 29, 2019

(54) SYNTHESIS OF INHIBITORS OF EZH2

(71) Applicant: Constellation Pharmaceuticals, Inc., Cambridge, MA (US)

(72) Inventors: Rishi G. Vaswani, Lexington, MA (US); Michael Charles Hewitt, Somerville, MA (US)

(73) Assignee: Constellation Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 16/342,741

(22) PCT Filed: Oct. 18, 2017

(86) PCT No.: PCT/US2017/057114
§ 371 (c)(1),
(2) Date: Apr. 17, 2019

(87) PCT Pub. No.: WO2018/075598
PCT Pub. Date: Apr. 26, 2018

(65) Prior Publication Data
US 2019/0233375 A1 Aug. 1, 2019

Related U.S. Application Data

(60) Provisional application No. 62/410,113, filed on Oct. 19, 2016.

(51) Int. Cl.
*C07D 211/28* (2006.01)
*C07D 401/06* (2006.01)
*C07D 401/14* (2006.01)

(52) U.S. Cl.
CPC .......... *C07D 211/28* (2013.01); *C07D 401/06* (2013.01); *C07D 401/14* (2013.01)

(58) Field of Classification Search
CPC ... C07D 211/82; C07D 401/06; C07D 401/14
See application file for complete search history.

(56) References Cited

U.S. PATENT DOCUMENTS

| 4,738,971 | A | 4/1988 | Eriksoo et al. |
| 5,308,854 | A | 5/1994 | Hoffman, Jr. et al. |
| 7,838,520 | B2 | 11/2010 | Delorme et al. |
| 8,410,088 | B2 | 4/2013 | Kuntz et al. |
| 8,536,179 | B2 | 9/2013 | Miller et al. |
| 8,846,935 | B2 | 9/2014 | Duquenne et al. |
| 9,051,269 | B2 | 6/2015 | Albrecht et al. |
| 9,085,583 | B2 | 7/2015 | Albrecht et al. |
| 9,206,128 | B2 | 12/2015 | Albrecht et al. |
| 9,371,331 | B2 | 6/2016 | Albrecht et al. |
| 9,374,093 | B2 | 6/2016 | Pelley et al. |
| 9,409,865 | B2 | 8/2016 | Albrecht et al. |
| 9,469,646 | B2 | 10/2016 | Albrecht et al. |
| 9,745,305 | B2 | 8/2017 | Albrecht et al. |
| 9,969,716 | B2 | 5/2018 | Albrecht et al. |
| 9,980,952 | B2 | 5/2018 | Albrecht et al. |
| 10,016,405 | B2 | 7/2018 | Albrecht et al. |
| 2003/0207875 | A1 | 11/2003 | Gymer et al. |
| 2003/0229081 | A1 | 12/2003 | Maduskuie |
| 2004/0186138 | A1 | 9/2004 | Annoura et al. |
| 2005/0266473 | A1 | 12/2005 | Zhang et al. |
| 2006/0035938 | A1 | 2/2006 | Bladh et al. |
| 2007/0155744 | A1 | 7/2007 | Jones et al. |
| 2008/0027050 | A1 | 1/2008 | Terauchi et al. |
| 2008/0227826 | A1 | 9/2008 | Frechette et al. |
| 2008/0280917 | A1 | 11/2008 | Albrecht et al. |
| 2009/0029991 | A1 | 1/2009 | Stokes et al. |
| 2009/0075833 | A1 | 3/2009 | Chinnaiyan et al. |
| 2009/0270361 | A1 | 10/2009 | Ito et al. |
| 2010/0069630 | A1 | 3/2010 | Lee et al. |
| 2010/0222420 | A1 | 9/2010 | Chinnaiyan et al. |
| 2010/0261743 | A1 | 10/2010 | Londregan et al. |
| 2010/0298270 | A1 | 11/2010 | Keana et al. |
| 2011/0105509 | A1 | 5/2011 | Kaila et al. |
| 2011/0212946 | A1 | 9/2011 | Barrow et al. |
| 2012/0071418 | A1 | 3/2012 | Copeland et al. |
| 2012/0264734 | A1 | 10/2012 | Kuntz et al. |
| 2013/0040906 | A1 | 2/2013 | Kuntz et al. |
| 2013/0230511 | A1 | 9/2013 | Heymach et al. |
| 2013/0310379 | A1 | 11/2013 | Albrecht et al. |
| 2014/0107122 | A1 | 4/2014 | Kuntz et al. |
| 2014/0142083 | A1 | 5/2014 | Kuntz et al. |
| 2015/0259351 | A1 | 9/2015 | Albrecht et al. |
| 2015/0368229 | A1 | 12/2015 | Albrecht et al. |
| 2015/0376190 | A1* | 12/2015 | Albrecht .............. C07D 401/14 514/265.1 |
| 2016/0009718 | A1 | 1/2016 | Albrecht et al. |

(Continued)

FOREIGN PATENT DOCUMENTS

WO 2003/020722 A1 3/2003
WO 2003/079986 A2 10/2003
(Continued)

OTHER PUBLICATIONS

Abreu et al., DNA methylation: a promising target for the twenty-first century. Expert Opin Ther Targets. Aug. 2008;12(8):1035-47.
Amatangelo et al., Three-dimensional culture sensitizes epithelial ovarian cancer cells to EZH2 methyltransferase inhibition. Cell Cycle. Jul. 1, 2013;12(13):2113-9.
CAS Registry No. 1061629-12-6 (Jul. 15, 2014).
CAS Registry No. 1100242-53-2 (Jul. 15, 2014).
CAS Registry No. 1118826-71-3 (Jul. 15, 2014).
CAS Registry No. 1269034-31-2 (Jul. 15, 2014).
CAS Registry No. 1269039-62-4 (Jul. 15, 2014).
CAS Registry No. 1278089-62-5 (Jul. 15, 2014).
SAS Registry No. 1290560-58-5 (Jul. 15, 2014).
Extended European Search Report for Application No. 13746186.9, dated Aug. 5, 2015. 6 pages.
Fiskus et al., Combined epigenetic therapy with the histone methyltransferase EZH2 inhibitor 3-deazaneplanocin A and the histone deacetylase inhibitor panobinostat against human AML cells. Blood. Sep. 24, 2009;114(13):2733-43.

(Continued)

*Primary Examiner* — Timothy R Rozof
(74) *Attorney, Agent, or Firm* — McCarter & English, LLP; Steven G. Davis; Michael J. DeGrazia

(57) ABSTRACT

Provided herein are synthetic methods for the preparation of EZH2 inhibitors.

20 Claims, No Drawings

(56) References Cited

U.S. PATENT DOCUMENTS

| | | | |
|---|---|---|---|
| 2016/0185757 | A1 | 6/2016 | Albrecht et al. |
| 2016/0333016 | A1 | 11/2016 | Albrecht et al. |
| 2017/0056388 | A1 | 3/2017 | Albrecht et al. |
| 2018/0037568 | A1 | 2/2018 | Albrecht et al. |

FOREIGN PATENT DOCUMENTS

| | | | |
|---|---|---|---|
| WO | 2007/011626 A2 | 1/2007 | |
| WO | 2007/014838 A1 | 2/2007 | |
| WO | 2007/067968 A2 | 6/2007 | |
| WO | 2009/006577 A2 | 1/2009 | |
| WO | 2009/087285 A1 | 7/2009 | |
| WO | 2009/153721 A1 | 12/2009 | |
| WO | 2011/131741 A1 | 10/2011 | |
| WO | 2011/140324 A1 | 11/2011 | |
| WO | 2011/140325 A1 | 11/2011 | |
| WO | 2012/005805 A1 | 1/2012 | |
| WO | 2012/024543 A1 | 2/2012 | |
| WO | 2012/051492 A2 | 4/2012 | |
| WO | 2012/068589 A2 | 5/2012 | |
| WO | 2012/075080 A1 | 6/2012 | |
| WO | 2012/115885 A1 | 8/2012 | |
| WO | 2012/118812 A2 | 9/2012 | |
| WO | 2013/039988 A1 | 3/2013 | |
| WO | 2013/049770 A2 | 4/2013 | |
| WO | 2013/067296 A1 | 5/2013 | |
| WO | 2013/067300 A1 | 5/2013 | |
| WO | 2013/067302 A1 | 5/2013 | |
| WO | 2013/075083 A1 | 5/2013 | |
| WO | 2013/075084 A1 | 5/2013 | |
| WO | 2013/078320 A1 | 5/2013 | |
| WO | 2013/120104 A2 | 8/2013 | |
| WO | 2013/138361 A1 | 9/2013 | |
| WO | 2013/155317 A1 | 10/2013 | |
| WO | 2013/155464 A1 | 10/2013 | |
| WO | 2013/173441 A2 | 11/2013 | |
| WO | 2014/049488 A1 | 4/2014 | |
| WO | 2014/062720 A2 | 4/2014 | |
| WO | 2014/062733 A2 | 4/2014 | |
| WO | 2014/071109 A1 | 5/2014 | |
| WO | 2014/077784 A1 | 5/2014 | |
| WO | 2014/085666 A1 | 6/2014 | |
| WO | 2014/092905 A1 | 6/2014 | |
| WO | 2014/097041 A1 | 6/2014 | |
| WO | 2014/100080 A1 | 6/2014 | |
| WO | 2014/124418 A1 | 8/2014 | |
| WO | 2014/151142 A1 | 9/2014 | |
| WO | 2015/023915 A1 | 2/2015 | |
| WO | 2015/200650 A1 | 12/2015 | |

OTHER PUBLICATIONS

Fiskus et al., Histone deacetylase inhibitors deplete enhancer of zeste 2 and associated polycomb repressive complex 2 proteins in human acute leukemia cells. Mol Cancer Ther. Dec. 2006;5(12):3096-104.

Gillet et al., The clinical relevance of cancer cell lines. J Natl Cancer Inst. Apr. 3, 2013;105(7):452-8.

Gura, Systems for identifying new drugs are often faulty. Science. Nov. 7, 1997;278(5340):1041-2.

Ito et al., A medium-term rat liver bioassay for rapid in vivo detection of carcinogenic potential of chemicals. Cancer Sci. Jan. 2003;94(1):3-8.

International Search Report for Application No. PCT/US2013/025639, dated May 8, 2013, 9 pages.

Johnson et al., Relationships between drug activity in NCI preclinical in vitro and in vivo models and early clinical trials. Br J Cancer. May 18, 2001;84(10):1424-31.

Knutson et al., Selective inhibition of EZH2 by EPZ-6438 leads to potent antitumor activity in EZH2-mutant non-Hodgkin lymphoma. Mol Cancer Ther. Apr. 2014;13(4):842-54.

Knutson et al., A selective inhibitor of EZH2 blocks H3K27 methylation and kills mutant lymphoma cells. Nat Chem Biol. Nov. 2012;8(11):890-6.

Knutson et al., Durable tumor regression in genetically altered malignant rhabdoid tumors by inhibition of methyltransferase EZH2. Proc Natl Acad Sci U S A. May 7, 2013;110(19):7922-7.

Konze et al., An orally bioavailable chemical probe of the Lysine Methyltransferases EZH2 and EZH1. ACS Chem Biol. 2013;8(6):1324-34.

McCabe et al., EZH2 inhibition as a therapeutic strategy for lymphoma with EZH2-activating mutations. Nature. Dec. 6, 2012;492(7427):108-12.

National Cancer Institute. Seer Training Modules. Cancer Classification. Retrieved online at: http://training.seer.cancer.gov/module_ase/unit3_categories2_by_histology.html. 3 pages. (2012).

PubChem Compound Summary for CID 40170690, May 30, 2009, 2 pages.

PubChem Compound Summary for CID 50961558, Mar. 29, 2011, 2 pages.

PubChem Compound Summary for CID 6918837, Jul. 28, 2006, 2 pages.

PubChem Compound Summary for CID 73087, Aug. 1, 2005, 2 pages.

Qi et al., Selective inhibition of Ezh2 by a small molecule inhibitor blocks tumor cells proliferation. Proc Natl Acad Sci U S A. Dec. 26, 2012;109(52)21360-5.

Registry, May 25, 2011, RN: 1300453-83-1.

Registry, Sep. 1, 2011, RN: 1326727-17-6.

Registry, Sep. 2, 2011, RN: 1327055-57-1.

Registry, Sep. 29, 2011, RN: 1333889-30-7.

Registry, Sep. 4, 2011, RN: 1328132-30-4.

Registry, Sep. 5, 2011, RN: 1328462-28-7.

Registry, Sep. 6, 2011, RN 1328976-87-9.

Registry, Sep. 7, 2011, RN 1329352-49-9.

Registry, Sep. 7, 2011, RN: 1329234-68-5.

Simone, Introduction. Omenn, Cancer Prevention. Part XIV, Oncology. Cecil Textbook of Medicine. 20th Edition, vol. 1. J. Claude Bennett (Ed.). W.B. Saunders Company. pp. 1004-1010. (1966).

Spannhoff et al., The emerging therapeutic potential of histone methyltransferase and demethylase inhibitors. ChemMedChem. Oct. 2009;4(10):1568-82.

STN registry database compound 1002886-67-0 from the ZINC (Soichet Laboratory) (entered STN on Feb. 12, 2008).

STN registry database compound 950111-40-7 from Chemical Library Supplier Enamine (entered STN on Oct. 10, 2007).

STN registry database compound 322425-80-9 (entered STN on Feb. 20, 2001).

Van Aller et al., Long residence time inhibition of EZH2 in activated polycomb repressive complex 2. ACS Chem Biol. Mar. 21, 2014;9(3):622-9.

Vazquez, Optimization of personalized therapies for anticancer treatment. BMC Syst Biol. Apr. 12, 2013;7:31. 11 pages.

Venkatesh et al., Role of the development scientist in compound lead selection and optimization. J Pharm Sci. Feb. 2000;89(2):145-54.

Verma et al., Identification of Potent, Selective, Cell-Active Inhibitors of the Histone Lysine Methyltransferase EZH2. ACS Med Chem Lett. Oct. 19, 2012;3(12):1091-6.

Williams et al., Foye's Principles of Medicinal Chemistry, 5th edition, Lippincott Williams & Wilkins. pp. 50, 59-61, (2002).

Woo et al., Biological evaluation of tanshindiols as EZH2 histone methyltransferase inhibitors. Bioorg Med Chem Lett. Jun. 1, 2014;24(11):2486-92.

Yap et al., Somatic mutations at EZH2 Y641 act dominantly through a mechanism of selectively altered PRC2 catalytic activity, to increase H3K27 trimethylation. Blood. Feb. 24, 2011;117(8):2451-9.

* cited by examiner

SYNTHESIS OF INHIBITORS OF EZH2

RELATED APPLICATIONS

This application is a U.S. national stage filing under 35 U.S.C. § 371 based on International Application No. PCT/US2017/057114, filed Oct. 18, 2017, which claims the benefit of priority to U.S. Provisional Application No. 62/410,113, filed Oct. 19, 2216, the contents of each of which are incorporated herein by reference.

BACKGROUND

Inhibitors of Enhancer of Zeste Homolog (EZH2) are promising drugs for the treatment of various cancers. See e.g., WO 2013/120104 and WO 2014/124418. Of particular importance due to their heightened activity for EZH2 are those inhibitors which, among other structural features, contain a chiral center between a substituted piperidinyl and indolyl moiety. See e.g., (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide described in U.S. Pat. No. 9,085,583. Economical and efficient means for preparing these stereoselective inhibitors are needed.

SUMMARY

Disclosed herein are economical and efficient methods for the preparation of EZH2 inhibitors and related intermediates. In one aspect, an EZH2 inhibitor of the formula:

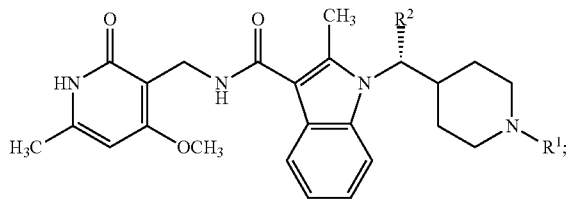

is stereoselectively prepared from a diastereomerically enriched sulfinamide compound having the formula:

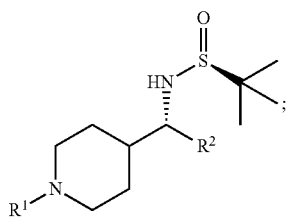

wherein the variables $R^1$ and $R^2$ are as described herein. This diastereomerically enriched sulfonamide can be prepared in approximately a 3:1 ratio of the desired S-absolute configuration (e.g., about 75% dr) over five steps from readily available starting materials. See Scheme 2. In addition, the sulfinyl group can be cleaved near quantitatively to afford the resulting amine. The resulting amine can then be optionally resolved as a chiral salt to improve the enantiomeric excess of the preferred enantiomer (e.g., >99% ee). This process can be performed on large scale (>25 kg) using commercially available reagents.

DETAILED DESCRIPTION

Provided herein is a method for preparing an EZH2 inhibitor having the Formula I:

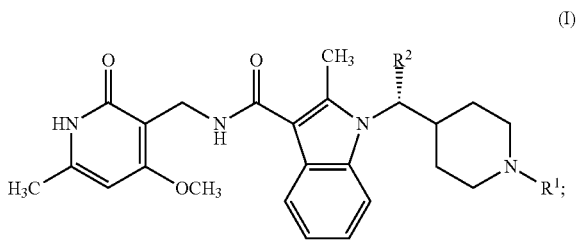

wherein $R^1$ is halo($C_1$-$C_6$)alkyl and $R^2$ is ($C_1$-$C_6$)alkyl.

Definitions

The term "optically active" means that the compound associated with this term rotates the vibrational plane of plane polarized light, i.e., the compound is not achiral. Typically, the compound is an enantiomer which is enantiomerically enriched over the possible enantiomer.

The term "diastereomerically enriched" means that the depicted diastereomer is present in excess over all other possible diastereomers. The diastereomeric excess of the depicted diastereomer can be e.g., at least 55%, at least 60%, at least 70%, at least 80%, at least at least 90%, at least 95%, at least 97%, at least 99% or at least 99.9% by weight over all other possible diastereomers.

The term "enantiomerically enriched" means that the depicted enantiomer is present in excess over the other possible enantiomer. The enantiomeric excess of the depicted enantiomer can be e.g., at least 55%, at least 60%, at least 70%, at least 80%, at least at least 90%, at least 95%, at least 97%, at least 99% or at least 99.9% by weight over the other possible enantiomer.

Diastereomeric excess (de) is defined as $|D_1-D_2|$ [(and the percent diastereomeric excess as $100(D_1-D_2)$], where $D_1$ is the mole fraction of the depicted diastereomer and $D_2$ is the mole fraction of all other possible diastereomers.

Enantiomeric excess (ee) is defined as $|F_{(+)}-F_{(-)}|$ (and the percent enantiomer excess by $100|F_{(+)}-F_{(-)}|$), where the mole fractions of two enantiomers are $F_{(+)}$ and $F_{(-)}$ (where $F_{(+)}+F_{(-)}=1$).

Unless indicated otherwise, when a particular enantiomer of a compound is named or depicted by structure, that enantiomer is present in an enantiomeric excess of at least 55%, at least 60%, at least 70%, at least 80%, at least at least 90%, at least 95%, at least 97%, at least 99% or at least 99.9% over the other possible enantiomer. Similarly, unless indicated otherwise, when a particular diastereomer of a compound is named or depicted by structure, that diastereomer is present in a diastereomeric excess of at least 55%, at least 60%, at least 70%, at least 80%, at least 90%, at least 95%, at least 97%, at least 99% or at least 99.9% over all other possible diastereomers.

Preparation of the Optically Active Acid/Indole

In a first step of the preparation of the optically active acid indole a secondary amine compound of the formula:

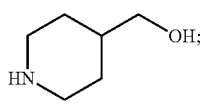

is reacted with $R^1$-L, where L is a leaving group, to form an alcohol compound of the formula:

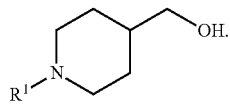

$R^1$ in the alcohol compound is as defined above for Formula I. The leaving group for this reaction is a molecular fragment that upon reaction with the secondary amine, departs with a pair of electrons in heterolytic bond cleavage. Leaving groups are known to those skilled in the art and include, but are not limited to halides (Cl, Br, or I) and sulfonate esters (e.g., mesylate, triflate, tosylate, methyl sulfate, and the like). In one aspect, the leaving group L in the formula $R^1$-L is a triflate, e.g., $R^1$-L is $R^1$—$O(SO_2)CF_3$. In one aspect, at least one equivalent of $R^1$-L is used.

The reaction can optionally be carried out in the presence of base. For example, a carbonate base (e.g., $K_2CO_3$, $KHCO_3$, $Na_2CO_3$, $NaHCO_3$, $Na_3H(CO_3)_2$, $Li_2CO_3$, $LiHCO_3$, $MgCO_3$, $Mg(HCO_3)_2$, $CaCO_3$, $Ca(HCO_3)_2$, and the like) may be used. Other examples include non-nucleophilic bases and/or sterically hindered bases such as N,N-diisopropylethylamine, 1,8-Diazabicycloundec-7-ene, 2,6-Di-tert-butylpyridine, 2,6-lutidine, dimethylaminopyridine, and pyridine. In one aspect, the leaving group is triflate such that $R^1$-L is of the formula: $R^1$—$O(SO_2)CF_3$ and the base is $K_2CO_3$. In one aspect, at least one equivalent of base relative to the secondary amine compound is used is used. Appropriate solvents for this reaction would be apparent to one of skill in the art. In one aspect, the solvent is an alcoholic solvent such as t-amyl alcohol, benzyl alcohol, butanol, t-butyl alcohol, ethanol, isobutanol, isopropyl alcohol, methanol, 1-propanol, and the like. In one aspect the solvent used in the reaction between the secondary amine compound and $R^1$-L is isopropanol.

In a second step, the alcohol compound of the formula:

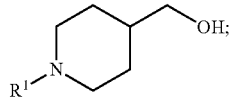

is oxidized with an oxidizing agent to the corresponding aldehyde compound of the formula:

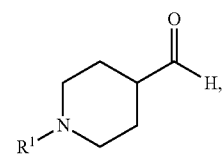

wherein $R_1$ is as defined defined above for Formula I.

Exemplary oxidizing reagents for this reaction include e.g., Pyridinium chlorochromate, pyridinium dichromate; chromium(VI) oxide with pyridine in dichloromethane; chromium trioxide in dilute sulfuric acid and acetone; DMSO and oxalyl chloride; dimethyl sulfoxide (DMSO) activated with a carbodiimide, such as dicyclohexylcarbodiimide; dimethyl sulfide ($Me_2S$) is treated with N-chlorosuccinimide (NCS), TEA; Dess-Martin periodinane, 2-iodoxybenzoic acid, tetrapropylammonium perruthenate optionally in the presence of N-Methylmorpholine N-oxide and (2,2,6,6-Tetramethylpiperidin-1-yl)oxyl (akaTEMPO)-derived reagents. In one aspect, the oxidizing agent is TEMPO and (diacetoxyiodo)benzene $PhI(OAc)_2$. TEMPO is typically present in catalytic amounts. Suitable solvents for this reaction would be apparent to one of skill in the art and include halogenated solvents such as methylene chloride, carbon tetrachloride, chloroform, dichloroethane, and the like. Although, in one aspect, the solvent used is methylene chloride. In one aspect, at least on equivalent of $PhI(OAc)_2$ relative to the alcohol compound is used.

In a third step, the aldehyde compound of the formula:

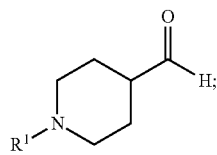

is reacted with an optically active sulfoxide compound of the formula:

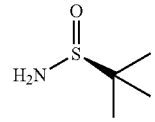

to form an optically active sulfinylimine compound of the formula:

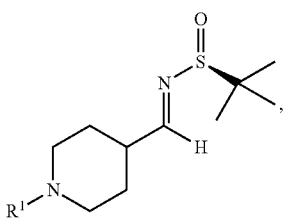

wherein $R_1$ is as defined above for Formula I.

This chiral sulfoxide in the sulfinylimine compound acts as a chiral auxillary to induce the desired stereochemistry at the imine carbon during the subsequent Grignard addition to form the diastereomerically enriched sulfinamide. Typically, the chiral sulfoxide is present in at least one equivalent relative to the aldehyde compound. The optically active sulfoxide compound

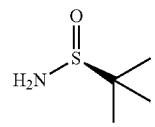

has an enantiomeric excess of >90% such as e.g., >95, >96%, >97%, >98%, >99%, >99.5%, or >99.9%. The reaction between the aldehyde and the optically active sulfoxide compound to form the sufinylimine compound can be carried out in the presence of a base e.g., a carbonate base (e.g., $K_2CO_3$, $KHCO_3$, $Na_2CO_3$, $NaHCO_3$, $Na_3H(CO_3)_2$, $Li_2CO_3$, $LiHCO_3$, $MgCO_3$, $Mg(HCO_3)_2$, $CaCO_3$, $Ca(HCO_3)_2$, and the like). Typically, the amount of carbonate base present is from 1 to 2 equivalents relative to the aldehyde compound. Alkoxide and amine bases can also be used e.g., titanium isopropoxide, potassium tert-butoxide, sodium methoxide, sodium ethoxide, triethylamine, N,N-diisopropylethylamine, dimethylaminopyridine, and pyridine. In one aspect, the base is $K_2CO_3$. The reaction between the aldehyde and the optically active sulfoxide compound to form the sufinylimine compound can also be carried out in the presence of a Lewis acid (e.g., $ZnCl_2$, $BF_3$, $SnCl_4$, $AlCl_3$, $MeAlCl_2$, and the like) or protic acids (e.g., sulfuorous, phosphoric, carbonic, hydrosulfuric, oxalic, and the like).

Suitable solvents for this reaction would be apparent to one of skill in the art and include ethereal solvents such as diethyl ether, di-tert-butyl ether, diisopropyl ether, 1,4-dioxane, dimethoxy ethane, dimethoxy methane, diglyme, ethyl tert-butyl ether, methyl tert-butyl ether, tetrahydrofuran, tetrahydropyran, and the like. In one aspect, the solvent used is tetrahydrofuran. Because bonds to the chiral sulfur atom are not broken, the sufinylimine compound has an enantiomeric excess of >90% such as e.g., >95, >96%, >97%, >98%, >99%, >99.5%, or >99.9%.

In a fourth step, the sulfinylimine compound of the formula:

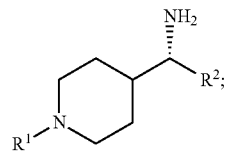

is reacted with a Grignard reagent having the formula $R^2MgX$, where X is bromide, iodide, or chloride; and $R^2$ is as described in the first embodiment to form a diastereomerically enriched sulfinamide compound having the formula:

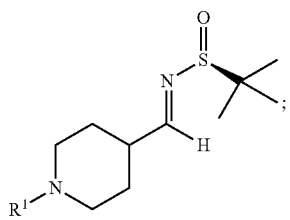

wherein $R^1$ and $R^2$ are as described above for Formula I. Typically at least 1.5 equivalents of Grignard reagent is used. Suitable solvents for this reaction would be apparent to one of skill in the art and include Grignard compatible solvents such as ethereal solvents (e.g., diethyl ether, di-tert-butyl ether, diisopropyl ether, 1,4-dioxane, dimethoxy ethane, dimethoxy methane, diglyme, ethyl tert-butyl ether, methyl tert-butyl ether, tetrahydrofuran, tetrahydropyran, and the like). In one aspect, the solvent used is tetrahydrofuran. The stereoselectivity of this reaction generally produces about a 3:1 ratio favoring the desired sulfinamide compound with S-absolute configuration.

In a fifth step, the sulfinyl group of the diastereomerically enriched sulfinamide compound is hydrolyzed e.g., by reacting it with acid to form an optically active amine compound of the formula:

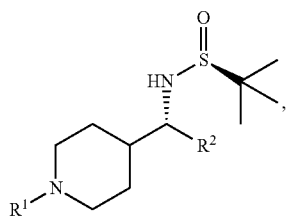

wherein $R^1$ and $R^2$ are as described above for Formula I. Hydrolysis of the sulfonamide for example by acidic removal of the sufinyl group is known to those skilled in the art and can be achieved e.g., using inorganic acids (such as HCl) with an alcoholic solvent such as isopropanol.

To remove the undesired enantiomer, the optically active amine can be reacted with an optically active organic acid to prepare a pair of diastereomeric salts comprising the optically active amine compound and the optically active acid, and the enantiomer of the optically active amine and the optically active acid. The optically active organic acids are typically of high optical purity (e.g., with enantiomeric excesses of greater than 98% such as e.g., >99%, >99.5%, and >99.9%). The reaction with the amine forms a pair of diastereomers (one having the desired stereochemistry), which can then be separated by conventional techniques. For example, in one instance the diastereomers can be separated via crystallization from a suitable solvent. The diastereomeric excess after separation (e.g., crystallization) is typically greater than 97% such as e.g., >98% or >99%. Neutralization of the separated salt of the optically active amine with base regenerates the optically active amine in higher optical purity than before the chiral resolution, typically with an enantiomeric excesses of greater than 99% ee).

Optically active acids that are capable of forming a chiral salt complex with the intended compound are known to one of skill in the art. For example, in the above chiral resolution, the optically active organic acid can be selected from aspartic acid, mandelic acid, camphanic acid, camphoric acid, camphorsulfonic acid, tartaric acid, glutamic acid, maleic acid, menthyloxyacetic acid, and methoxyphenylacetic acid. In one aspect, the optically active acid is a mandelic acid such that the resulting diastereomeric salt comprising the optically active amine compound and the optically active organic acid has the following formula:

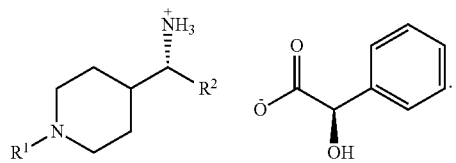

In a sixth step, the optically active amine or a salt form of the optically active amine including the diastereomeric salt form used in the chiral resolution is then reacted with a di-keto ester compound having the formula:

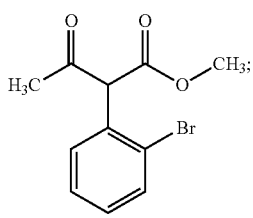

to form an optically active enamine compound of the formula:

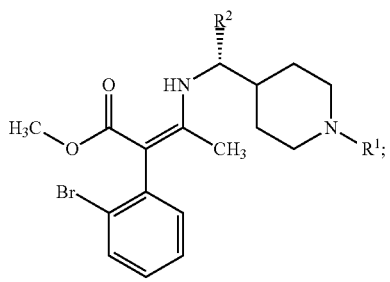

or a salt thereof, wherein R¹ is defined above for Formula I. Appropriate solvents for this reaction would be apparent to one of skill in the art and include, in some aspects, those with boiling points above 65° C., e.g., isopropyl acetate, acetonitrile, dimethyl-formamide, benzene, cyclohexane, 1,2-dichloroethane, glyme, ethyl acetate, hexamethylphosphorous triamide, hexamethylphosphoramide, dimethyl sulfoxide, and toluene. To facilitate formation of the enamine, the reaction may be performed at temperatures ranging from room temperature to 120° C. In one aspect the reaction is performed in isopropyl acetate at reflux.

Cyclization to an optically active indole compound of the formula:

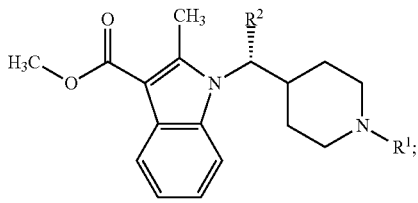

or a salt thereof, wherein R¹ and R² are is defined above for Formula I, occurs under palladium-mediated cyclization conditions. See e.g., *Org. Lett.*, 2014, 16 (16), pp 4114-4117. For example, cyclization can occur in the presence of palladium(II) catalysts (e.g., bis(acetonitrile)palladium(II) chloride, palladium(II) acetate, palladium(II) bromide, palladium(II) chloride, palladium(II) trifluoroacetate, tetrakis (acetonitrile)palladium (II) tetrafluoroborate, [1,2-bis(diphenylphosphino)ethane] dichloropalladium(II), bis(triethylphosphine)palladium(II) chloride, bis(triphenylphosphine)palladium(II) acetate, bis(triphenylphosphine)palladium(II) chloride, bis[tri(o-tolyl)phosphine]palladium(II) chloride, dichlorobis(tricyclohexylphosphine)palladium(II), trans-benzyl (chloro) bis(triphenylphosphine)palladium(II), and the like or commercially available palladium(0) catalysts (e.g., tris(dibenzylideneacetone)dipalladium(0), bis(tricyclohexylphosphine) palladium(0), bis(tri-t-butylphosphine) palladium(0), bis[1,2-bis(diphenylphosphino)ethane] palladium(0), tetrakis(triphenylphosphine)palladium(0), and the like. In one aspect, the palladium catalyst used in the cyclization is tris(dibenzylidene acetone) dipalladium(0).

Ligands for use in facilitating palladium-mediated cyclizations may also be used. See e.g., *Org. Lett.*, 2014, 16 (16), pp 4114-4117. Typically, ligands are used in catalytic amounts and may be selected from a monodentate or bidentate ligands. Examples of monodentate ligands include, but are not limited to, general ligands (e.g., triphenylphosphine, tri-(2-furyl)phosphine, tri-o-tolylphosphine, trimesitylphosphine, tricyclohexylphosphine, tri-tert-butylphosphine tetrafluoroborate, triisopropylphosphine, tri-n-butylphosphine, di-tert-butylmethylphosphine, and tri-tert-butylphosphine), Buchwald-type ligands (e.g., 2-(dicyclohexylphosphino)-2'-isopropylbiphenyl, 2-(dicyclohexylphosphino)-2',4',6'-triisopropylbiphenyl, 2-(di-tert-butylphosphino)biphenyl, 2-(dicyclohexylphosphino) biphenyl, 2-dicyclohexylphosphino-2'-(N,Ndimethylamino)biphenyl, 2-diphenylphosphino-2'-(N,Ndimethylamino)biphenyl, 2-(dicyclohexylphosphino)-2'-methylbiphenyl, 2-(di-tert-butylphosphino)-2'-methylbiphenyl, 2-di-tert-butylphosphino-2'-(N,Ndimethylamino) biphenyl, 2-dicyclohexylphosphino-2',6'-diisopropoxyl,1'-biphenyl, and 2-di-tert-butylphosphino-2',4',6'-triisopropylbiphenyl), and NHC ligands (e.g., 1,3-bis(2,4,6-trimethylphenyl)imidazolium chloride,1,3-bis(2,6-diisopropylphenyl)imidazolium chloride, 1,3-bis(adamant-1-yl) imidazolium chloride, 1,3-bis(2,4,6-trimethylphenyl)-4,5-dihydroimidazolium tetrafluoroborate, 1,3-bis(2,6-diisopropylphenyl) imidazolidinium tetrafluoroborate, 1,3-bis(2,4,6-trimethylphenyl) imidazolidinium chloride, and 1,3-bis(2,6-diisopropylphenyl) imidazolidinium chloride. Examples of bidendate ligands include, but are not limited to, general ligands (e.g., bis(diphenylphosphino)methane, 1,2-bis(diphenylphosphino)ethane, 1,2-bis(dicyclohexylphosphino) ethane, 1,3-bis(diphenylphosphino)propane, 1,3-bis(dicyclohexylphosphino)propane, 1,4-bis(diphenylphosphino) butane, 1,5-bis(diphenylphosphino)pentane, bis(2-diphenylphosphinophenyl)ether, 1,1'-bis(diphenylphosphino) ferrocene, 1,1'-bis(diisopropylphosphino)ferrocene, 1,1'-bis (di-tert-butylphosphino)ferrocene, 1,2-bis(diphenylphosphino)benzene, and 9,9-dimethyl-4,5-bis(diphenylphosphino)xanthene), BINAP ligands (e.g., (S)-(−)-2,2'-bis (di-p-tolylphosphino)-1,1'-binaphthyl, (R)-(+)-2,2'-bis(di-p-tolylphosphino)-1,1'-binaphthyl, (S)-(−)-2,2'-bis(diphenylphosphino)-1,1'-binaphthyl, (R)-(+)-2,2'-bis(diphenylphosphino)-1,1'-binaphthyl, rac-2,2'-bis(di-p-tolylphosphino)-1,1'-binaphthyl, rac-2,2'-bis(di(3,5-dimethylphenyl) phosphino)-1,1'-binaphthyl, and (±)-2,2'-bis(diphenylphosphino)-1,1'-binaphthyl), and Josiphos ligands (e.g., (R)-(−)-1-[(S)-2-di-t-butylphosphino) ferrocenyl]ethyldi-(4-trifluoromethylphenyl) phosphine, (R)-(−)-1-[(S)-2-diphenylphosphino) ferrocenyl]ethylbis(3,5-dimethylphenyl)phosphine, (R)-(−)-1-[(S)-2-dicyclohexylphosphino) ferrocenyl] ethyldicyclohexylphosphine, (R)-(−)-1-[(S)-2-diphenylphosphine)ferrocenyl] ethyldi-tert-butylphosphine, and (R)-(−)-1-[(S)-2-diphenylphosphino) ferrocenyl]ethyldicyclohexylphosphine). In one aspect, the ligand tri-tert-butylphosphine tetrafluoroborate is used in the cyclization to form the enamine.

Suitable solvents that can be used for palladium-mediated cyclizations are known and include e.g., ethereal (diethyl ether, di-tert-butyl ether, diisopropyl ether, 1,4-dioxane, dimethoxy ethane, dimethoxy methane, diglyme, ethyl tert-butyl ether, methyl tert-butyl ether, tetrahydrofuran, tetrahydropyran, and the like), alcoholic (e.g., t-amyl alcohol, benzyl alcohol, butanol, t-butyl alcohol, ethanol, isobutanol, isopropyl alcohol, methanol, 1-propanol, and the like), cyclic ureas (e.g., 1,3-Dimethyl-3,4,5,6-tetrahydro-2(1H)-pyrimidinone), and those with moderate to high boiling points (e.g., isopropyl acetate, acetonitrile, dimethylformamide, dimethyl sulfoxide, toluene, and the like). In one aspect, the solvent is 1,4-dioxane, t-butanol, acetonitrile, dimethoxyethane, 1,3-Dimethyl-3,4,5,6-tetrahydro-2(1H)-pyrimidinone, or ethanol.

Suitable bases that can be used for palladium-mediated cyclizations are known and include e.g., carbonate bases (e.g., $K_2CO_3$, $KHCO_3$, $Na_2CO_3$, $NaHCO_3$, $Na_3H(CO_3)_2$, $Li_2CO_3$, $LiHCO_3$, $MgCO_3$, $Mg(HCO_3)_2$, $CaCO_3$, $Ca(HCO_3)_2$, and the like) alkyl amine bases (such as trimethylamine, N,N,-diisopropylethylamine, n-BUNMe$_2$, and the like), and methoxide bases (such as NaOMe, NaOEt, and the like). In one aspect, the base is $Cs_2CO_3$, $K_2CO_3$, n-BUNMe$_2$, or NaOMe.

In a seventh step, the ester of the optically active indole compound is hydrolized to the free acid e.g., with hydroxide base to afford an active acid/indole compound of the formula:

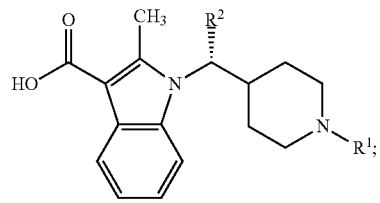

as described above in the first embodiment. The hydrolysis can be performed according to conditions knows to one of skill in the art e.g., under aqueous basic conditions e.g., in the presence of hydroxide base (e.g., potassium hydroxide, lithium hydroxide, sodium hydroxide, magnesium hydroxide, calcium hydroxide,)ammonium hydroxide, and the like) in water optionally with an alcoholic solvent (e.g., t-amyl alcohol, benzyl alcohol, butanol, t-butyl alcohol, ethanol, isobutanol, isopropyl alcohol, methanol, 1-propanol, and the like). In one aspect, the hydrolysis is performed using potassium hydroxide in water and ethanol.

In an eighth step, the optically active acid/indole compound of the formula:

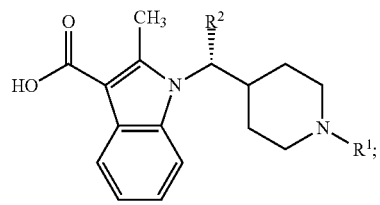

wherein $R_1$ and $R_2$ are as defined in the first step, is reacted with the free amine of a compound of the formula:

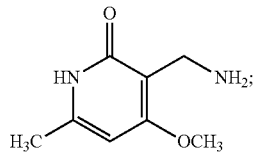

to generate the amide bond linkage in the optically active indole pyridine-one. The free amine compound can be prepared following the procedure set forth in WO 2013/120104 and as described The reaction can be performed under standard amide bond formation conditions that include e.g., the use of one or more carboxylic acid couple reagents. Carboxylic acid coupling reagents are known in the art and include e.g., carbodiimides, phosphonium reagents, aminium/uranium-imonium reagents, N-ethoxycarbonyl-2-ethoxy-1,2-dihydroquinoline, 2-propanephosphonic acid anhydride, 4-(4,6-dimethoxy-1,3,5-triazin-2-yl)-4-methylmorpholinium salt, bis-trichloromethylcarbonate, or 1,1'-carbonyldiimidazole. In one aspect, the coupling reagent used in the preparation of the optically active indole pyridine-one is 1,1'-carbonyldiimidazole. Suitable solvents for this reaction would be apparent to one of skill in the art and include ethereal solvents such as diethyl ether, di-tert-butyl ether, diisopropyl ether, 1,4-dioxane, dimethoxy ethane, dimethoxy methane, diglyme, ethyl tert-butyl ether, methyl tert-butyl ether, tetrahydrofuran, tetrahydropyran, and the like. In one aspect, the solvent used is tetrahydrofuran.

The preparation of the free amine compound described in the first embodiment, and having the formula:

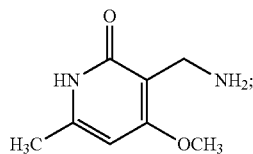

can be prepared following the procedure set forth in WO 2013/120104 and as described in the Exemplification section below.

Specific examples of synthetic methods described herein are provided in the Exemplification section below. Neutral forms as well as salts of the compounds described in the synthesis are included in the invention.

EXEMPLIFICATION

Scheme 1 below is a retrosynthetic analysis for forming EZH2 inhibitors comprising a chiral methylene bridging a substituted piperidinyl and indolyl moiety.

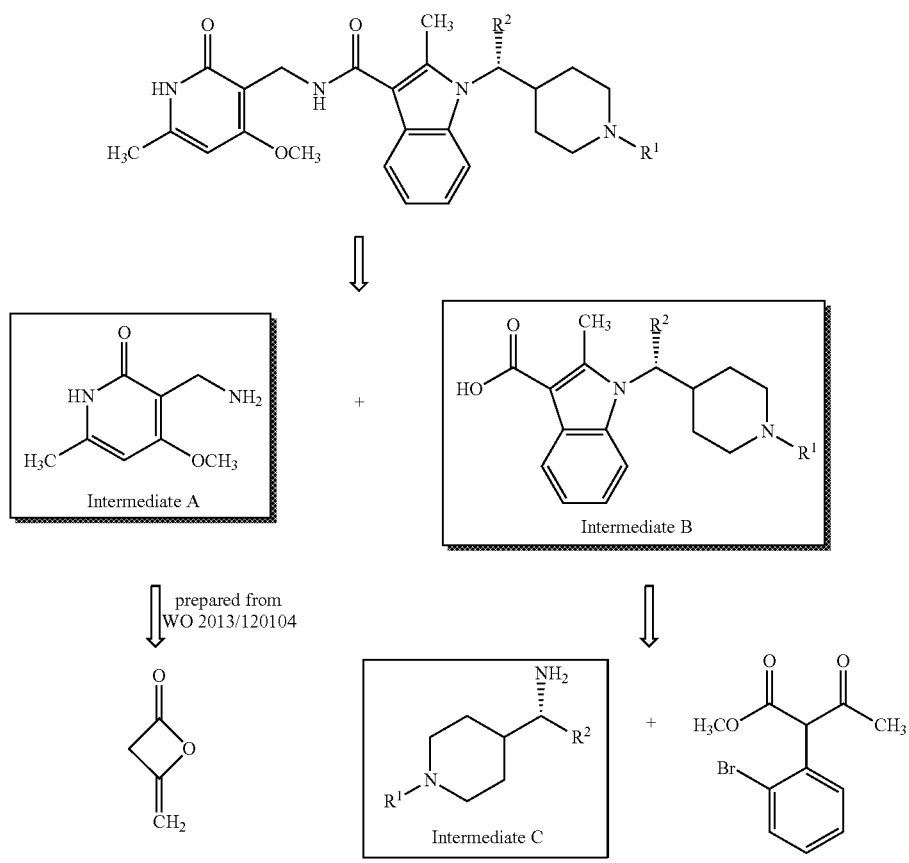
Scheme 2 illustrates an exemplary synthesis for Intermediate C as a mandelate salt, where $R^1$ is —CH$_2$CF$_3$, and $R^2$ is —CH$_3$.
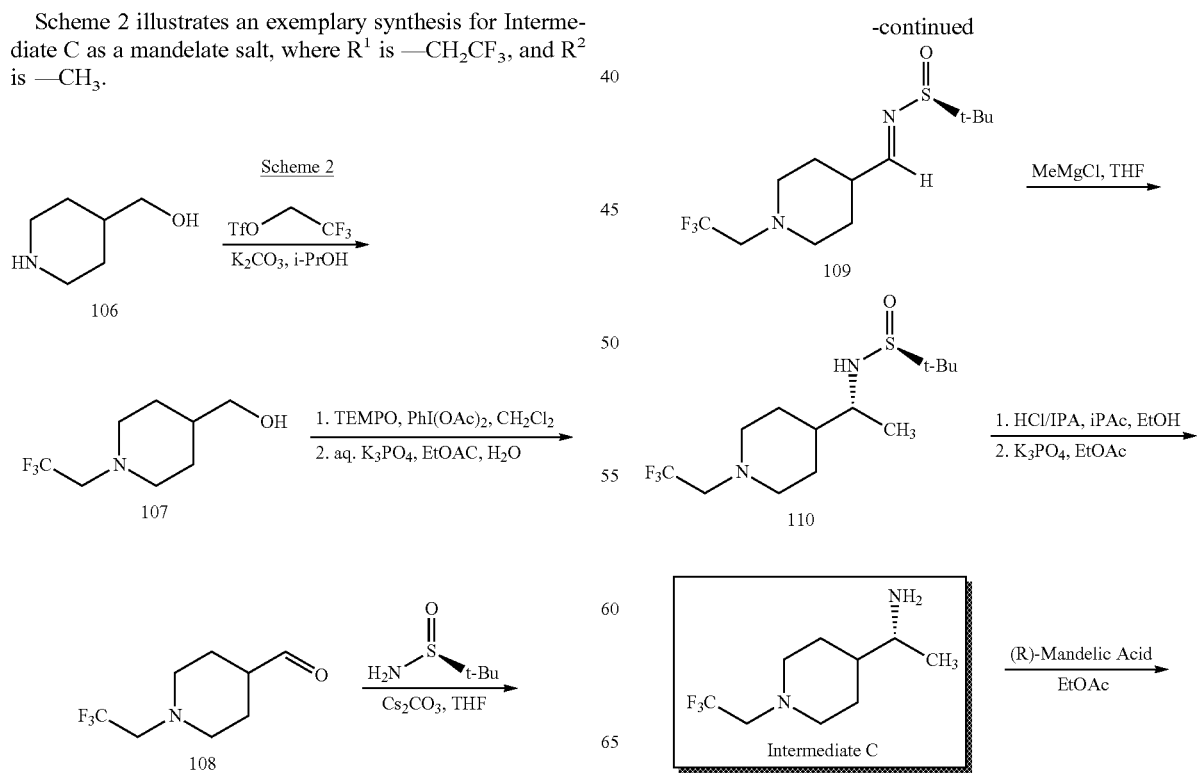

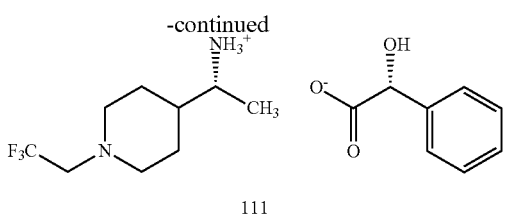

111

Preparation of (1-(2,2,2-trifluoroethyl)piperidin-4-yl)methanol 107

A 1000 L reactor was charged piperidin-4-ylmethanol 106 (46.7 Kg, 405 mol) and THF (292.8 Kg). The reactor was charged with K$_2$CO$_3$ (72.8 Kg) before adding 2,2,2-trifluoroethyl trifluoromethanesulfonate (94.0 Kg, 405 mol in 41.8 kg of THF) dropwise maintaining the temperature below 55° C. The mixture was warmed to 60-65° C. and stirred for 4 hrs before being allowed to cool down to ambient temperature. Methyl tert-butyl ether (MTBE) (104.3 kg) was then added and the mixture was stirred for 20 mins. The resulting solid was collected by filtration, rinsed by MTBE (104.3 kg). The filtrate was concentrated under vacuum, and then the cake was mixed with MTBE (104.3 kg), celite (23.5 kg) and PE (97.3 kg) and was stirred for 30 mins. Filtered and the cake was rinsed by MTBE/PE (1:1, 103.8 kg). The combined filtrate was concentrated to afford compound 107 as an oil (75.3 kg, 93.5 yield, 99.3% HPLC purity).

Preparation of 1-(2,2,2-trifluoroethyl)piperidine-4-carbaldehyde 108

A 500 L reactor was charged with (1-(2,2,2-trifluoroethyl)piperidin-4-yl)methanol 107 (75.3 Kg, 381 mol), DCM (299 kg) and TEMPO (11.9 Kg, 76 mol). Iodo-benzene-bis-acetate (147.6 Kg, 458 mol) was added portionwise, maintaining the temperature at 25-30° C. The reaction was stirred at ambient temperature for 2 hrs then cooled to 5-10° C. MTBE (666 kg) was added and 10 wt % aqueous Na$_2$S$_2$O$_3$ (300 kg) was slowly added, maintaining the temperature between 10 and 15° C. The mixture was stirred for 20 mins, treated with 40% aqueous NaOH aqueous (90.0 kg) at such a rate to maintain the temperature at 10-15° C., and pH was adjusted to 13-14. The layers were separated and the organic layer was washed with 2N HCl (300 kg) at 10-15° C. and then with brine (375 kg), dried over Na$_2$SO$_4$, filtered, and concentrated in vacuo to to afford crude aldehyde 108 as an oil (68.5 kg, 92% yield, 64.6% GC purity).

Preparation of (S,E)-2-methyl-N-((1-(2,2,2-trifluoroethyl)piperidin-4-yl)methylene)propane-2-sulfinamide 109

A 1000 L reactor was charged with 1-(2,2,2-trifluoroethyl)piperidine-4-carbaldehyde 108 (68.5 kg, 351 mol) and DCM (546.6 kg). (S)-2-methylpropane-2-sulfinamide (42.5 kg, 351 mol) was charged in portions follow by cesium carbonate (80 kg, 246 mol). The reaction was stirred at ambient temperature for 4 hrs. The slurry was filtered and the with DCM (273.3 kg). Concentration in vacuo afforded compound 109 as an oil (108 kg, 100% yield, 91.2% HPLC purity).

Preparation of (S)-2-methyl-N—((R)-1-(1-(2,2,2-trifluoroethyl)piperidin-4-yl)ethyl)propane-2-sulfinamide 110

A 2000 L reactor was charged THF (672.8 kg) under N$_2$ and with methylmagnesium chloride in THF (360 kg, 1038 mol). The mixture was cooled to −5° C. before adding (S,E)-2-methyl-N-((1-(2,2,2-trifluoroethyl)piperidin-4-yl)methylene)propane-2-sulfinamide 109 (108.0 kg, 362 mol) as a solution in THF (91.6 kg) and at such a rate as to maintain the temperature between −5 and 0° C. The mixture was stirred for 6 hrs and quenched with 20% NH$_4$Cl/deionized H$_2$O (1080 kg) before allowing the mixture to warm to ambient temperature. The organic phase was dried over anhydrous Na$_2$SO$_4$, filtered and concentrated in vacuo to provide compound 110 as an oil (100.0 kg, 89.0% yield, 83.7% HPLC purity).

Preparation of (R)-1-(1-(2,2,2-trifluoroethyl)piperidin-4-yl)ethan-1-amine (Intermediate C)

A 1000 L reactor was charged 11% hydrochloric acid in EtOH (115.4 kg). A solution of (S)-2-methyl-N—((R)-1-(1-(2,2,2-trifluoroethyl)piperidin-4-yl)ethyl)propane-2-sulfinamide 110 (42.7 Kg, 135.9 mol) in isopropylacetate (335.0 Kg) was then added over 3 hrs, maintaining the temperature between 20 and 25° C. After 1 hr, the resulting solid was collected by filtration and washed with isopropylacetate. The solids were transferred to a clean 1000 L reactor, and then K$_3$PO$_4$ (37% w/w, 271.0 kg) and EtOAc (135.0 Kg) were added. The mixture was thoroughly stirred and the layers were separated. The aqueous layer was extracted with EtOAc (2×135.0 Kg) and the combined organic phases were washed with brine (600 kg) and concentrated in vacuo to provide Intermediate C as an oil (19.0 kg).

Preparation of (R)-1-(1-(2,2,2-trifluoroethyl)piperidin-4-yl)ethan-1-aminium (R)-2-hydroxy-2-phenylacetate 111

The resulting oil from above (19.0 kg) was charged to a 1000 L reactor and diluted with ethyl acetate (171.0 kg). To the solution was added (R)-(−)-mandelic (16.5 kg), and the mixture was heated to 50-55° C. for 1 h. The slurry was cooled to ambient temperature and stirred for an additional 2 h. The slurry was filtered and washed with MTBE (33.0 kg), dried under vacuum at 45° C. to give the desired product (24.5 kg, ee 99.3%).

Scheme 3 illustrates an exemplary synthesis for Intermediate B, where R$^1$ is —CH$_2$CF$_3$, and R$^2$ is —CH$_3$.

Scheme 3

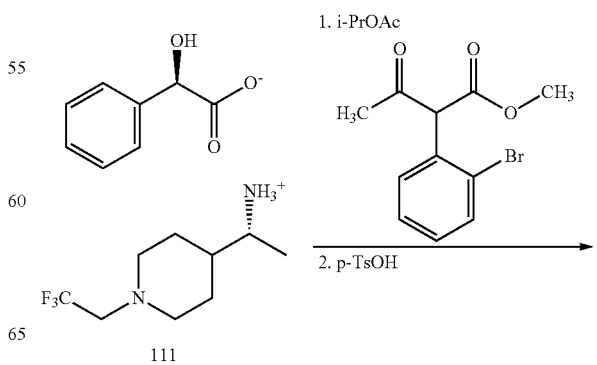

111

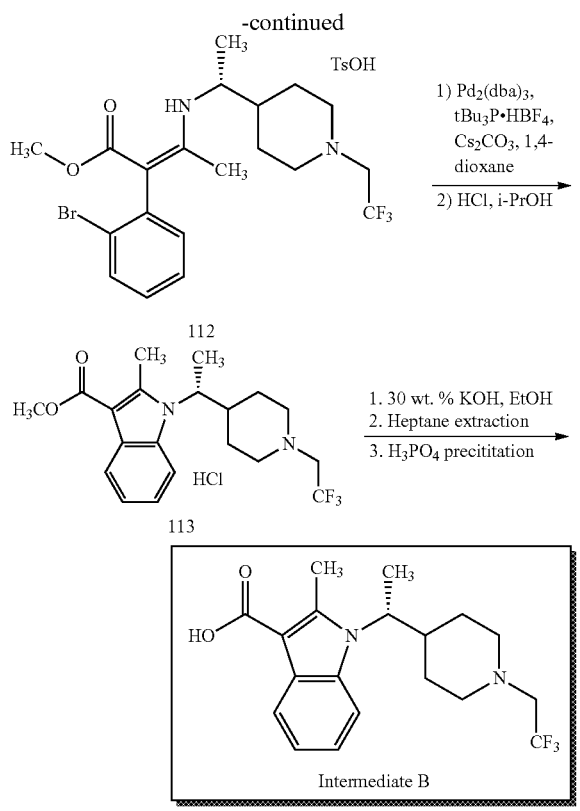

Preparation of Methyl (R,Z)-2-(2-bromophenyl)-3-((1-(1-(2,2,2-trifluoroethyl)piperidin-4-yl)ethyl)amino)but-2-enoate 4-methylbenzenesulfonate 112

A dry 100 L Büchi jacketed reactor was charged with (R)-1-(1-(2,2,2-trifluoroethyl)piperidin-4-yl)ethan-1-aminium (R)-2-hydroxy-2-phenylacetate 111 (6.0 kg, 16.56 mol), Methyl 2-(2-bromophenyl)-3-oxobutanoate (5.39 kg, 19.87 mol) and iPrOAc (42 L, 36.6 kg). To enable more efficient removal of water, MTBE (8 L, 5.9 kg) was charged to the reactor. The batch was agitated and heated to 85° C. Atmospheric distillation was utilized to collect approximately 20 L of solvent, and the reaction was sampled for progress. Completion of the enamine formation was confirmed by HPLC analysis. The batch was cooled to <40° C. and treated with a saturated solution of sodium bicarbonate (30 L). The batch was agitated for 5 min, and the phases were allowed to separate for 5 min before removing the bottom aqueous layer.

To the reactor was added saturated brine solution (NaCl in $H_2O$, 30 L) to wash the organics. The batch was agitated for 5 min, and the phases were allowed to separate for 5 min before removing the bottom aqueous layer. MTBE (4 L, 3.0 kg) was added to the reactor, and the batch was concentrated to an oil. iPrOAc (30 L, 26.6 kg) was charged and the reaction was polish filtered (20 μm inline cartridge) directly into a 150 L cylindrical reactor. Additional iPrOAc (50 L, 26.1 kg) was charged followed by TsOH.$H_2O$ (3.15 kg) to promote salt formation. The batch was agitated overnight at ambient temperature. The resulting slurry was filtered and washed with iPrOAc (30 L, 26.6 kg). The product was transferred to Teflon-lined trays and dried in a vacuum oven (270 mBar w/nitrogen bleed) at 45° C. until constant mass was achieved. Desired product 112 was obtained as a chalky, off-white solid (8.42 kg, 80% yield, 95.0 wt % purity).

Preparation of Methyl (R)-2-methyl-1-(1-(1-(2,2,2-trifluoroethyl)piperidin-4-yl)ethyl)-1H-indole-3-carboxylate hydrochloride 113

A dry 100 L Büchi jacketed reactor inerted with Argon was charged with $Cs_2CO_3$ (6.66 kg, 20.46 mol), Methyl (R,Z)-2-(2-bromophenyl)-3-((1-(1-(2,2,2-trifluoroethyl)piperidin-4-yl)ethyl)amino)but-2-enoate 4-methylbenzenesulfonate 112 (5.20 kg, 8.18 mol), $Pd_2(dba)_3$ catalyst (225 g, 0.245 mol), and Tri-tert-butylphosphonium tetrafluoroborate ligand (142 g, 0.491 mol). To the reactants was added 1,4-dioxane (41.6 L, 42.8 kg), which had been sparged with argon for 30 min prior to the addition. The reaction was heated >95° C. and agitated for >6 h to completion (100% conversion by HPLC analysis). The batch was cooled to 60° C. and Silicycle metal scavenger (1029 g, 30 wt %) was charged to the reactor to remove excess Pd metal catalyst. The slurry was agitated for 12-18 h and cooled to 20-25° C. The slurry was filtered over Celite and washed with 50:50 IPA/Heptane (4.66 kg/5.35 kg). The filtrate was then passed through a fritted glass funnel (6 L) packed with Celite underneath a layer of Silicycle metal scavenger. The resulting filtrate was charged into the clean 100 L Büchi reactor, and the solvent was removed under reduced pressure. After ~25 L of solvent was distilled, IPA (4 L, 3.1 kg) and Heptane (4 L, 2.7 kg) were charged to the reactor, and the distillation continued until ~27 L of solvent was removed. The batch was cooled to 20-25° C., IPA was charged (6.9 L, 5.39 kg), and the reaction was transferred through a cartridge filter (20 μm inline cartridge) into a 100 L RB flask equipped with temperature probe and batch concentrator. An addition funnel was used to charge 5 M HCl in IPA (1.8 L, 1.62 kg) dropwise.

Heptane (6.8 L, 4.66 kg) was added slowly to the reaction resulting in the precipitation of minor amounts of product. The reaction was seeded with target 113 crystals to promote seed bed formation. Additional heptane (6.8 L, 4.66 kg) was charged dropwise, and the reaction was agitated overnight. Heptane (13.6 L, 9.33 kg) was charged, and the reaction was concentrated under reduced pressure to remove 6 L of solvent. To the reaction was charged heptane (6 L, 4.1 kg) was charged dropwise, and the reaction was concentrated under reduced pressure to remove 14 L of solvent. Heptane (14 L, 9.6 kg) was charged dropwise. The slurry was sampled for loss to filtrate via HPLC analysis (result=2.9 mg/mL) and was further concentrated to remove an additional 6 L of solvent. Heptane (6 L, 4.1 kg) was charged to the reactor, and the slurry was agitated overnight. The slurry was again sampled for loss to filtrate (result=1.2 mg/mL), filtered, and washed with heptane (2×5.83 kg). The product was transferred to Teflon-lined trays and dried in a vacuum oven (270 mBar w/nitrogen bleed) at 50° C. until constant mass was achieved. Desired product 113 was obtained as an off-white solid (2.93 kg, 85% yield, 100 wt % purity).

Preparation of (R)-2-methyl-1-(1-(1-(2,2,2-trifluoroethyl)piperidin-4-yl)ethyl)-1H-indole-3-carboxylic acid (Intermediate B)

A dry 100 L Büchi jacketed reactor was charged with Methyl (R)-2-methyl-1-(1-(1-(2,2,2-trifluoroethyl)piperidin-4-yl)ethyl)-1H-indole-3-carboxylate hydrochloride 113 (3.50 kg, 8.36 mol) followed by KOH (7.00 kg, 30 wt %) and EtOH (17.5 kg, 190 proof). The reaction was heated to 75° C. and agitated for approximately 18 h to completion (100% conversion by HPLC). The batch was cooled to <25° C. and diluted with HPP water (9 vol., 31.5 kg). To the reactor was added heptane (17.5 L, 12 kg). The batch was agitated for 5 min and allowed to phase split for 5 min. The bottom aqueous layer was then transferred to a 100 L RB flask. Charcoal was charged to the reactor (350 g, 10 wt %). The slurry was heated to 50-60° C. and agitated for 2 h. The reaction was cooled to <25° C. and the slurry was pre-filtered over a tabletop funnel to remove a majority of the charcoal. The collected filtrate was then passed through a fritted glass funnel (6 L) packed with Celite (2-3" depth). The resulting filtrate was transferred into the clean 100 L Büchi reactor. To the reaction mixture was charged 2 M $H_3PO_4$ (approximately 18 L) with pH monitoring to achieve pH ~4.8 (calibrated pH probe). The slurry was then filtered and washed with HPP Water (2×17.5 kg). The product was transferred to Teflon-lined trays and dried in a vacuum oven (270 mBar w/nitrogen bleed) at 55° C. until constant mass was achieved. Intermediate B was obtained as an off-white solid (2.60 kg, 85% yield, 100 wt % purity).

Scheme 4 illustrates an exemplary synthesis of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (see e.g., U.S. Pat. No. 9,085,583) using Intermediate A and Intermediate B, where $R^1$ is —$CH_2CF_3$, and $R^2$ is —$CH_3$, as well as a subsequent crystallization or trituration step to form a solid form of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (see e.g., PCT/US2016/048616).

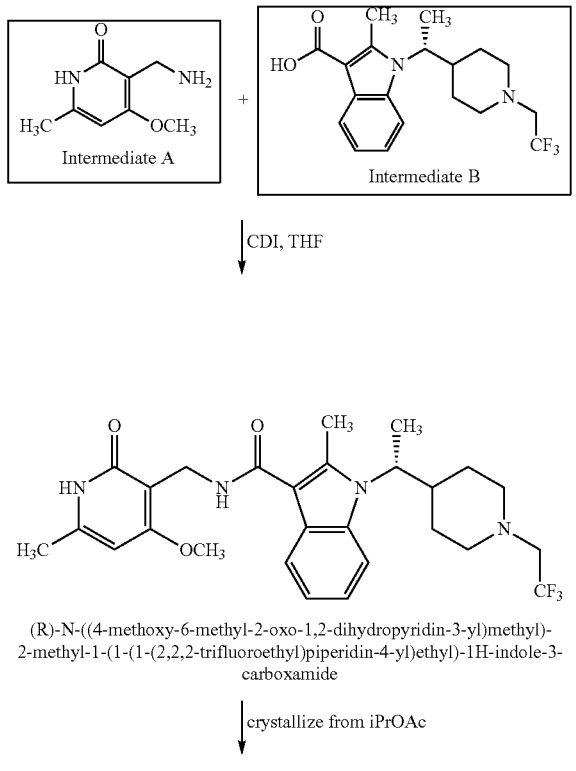

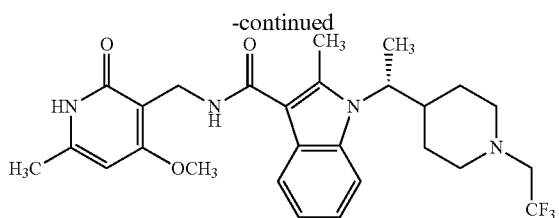

(R)-N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide
Form C (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (Coupling of Intermediate A with Intermediate B)

A dry 100 L Büchi jacketed reactor was charged with CDI (1.21 kg, 7.46 mol, 1.10 equiv.) followed by THF (12.5 L, 11.11 kg). The reaction was heated to 60±5° C. with agitation. A solution of (R)-2-methyl-1(1-(1-(2,2,2-trifluoroethyl)piperidin-4-yl)ethyl)-1H-indole-3-carboxylic acid (Intermediate B, 2.50 kg, 6.79 mol) in THF (10 L, 8.89 kg) was added slowly (~1.5 h) to the reactor via an addition funnel maintaining the temperature at 60±5° C. The reaction was agitated at 60±5° C. for ~3 h, after which a sample of the reaction was analyzed by HPLC (99% conversion to the acyl imidazole intermediate). To the reactor was added 3-(aminomethyl)-4-methoxy-6-methylpyridin-2(1H)-one (Intermediate A, 1.58 kg, 9.36 mol, 1.38 equiv), where THF (1.2 L, 1.11 kg) was used to aid in transfer. The reaction was agitated at 60±5° C. for 20 h to completion (>96% conversion by HPLC). The batch was then cooled to <30° C. and filtered. The reactor and funnel were rinsed with THF (2.5 L, 2.22 kg). The THF filtrate was transferred to a 100 L separatory funnel. To the separatory funnel was charged HPP water (12.5 kg, 5 vol.), and the reaction was diluted with iPrOAc (62.6 L, 54.5 kg).

The contents were agitated for 5 min, and the aqueous layer was removed. The organic layer was washed three additional times with water (3×12.5 kg, 5 vol.). After the four water washes, the organic layer was polish filtered through a cartridge filter (1 μm inline cartridge) and transferred back into the cleaned 100 L Büchi reactor. The organic layer was concentrated until approximately 18 L remained, and then iPrOAc (6.3 L, 5.45 kg) was charged to the reactor. The reaction was again concentrated until approximately 18 L remained, and iPrOAc (25 L, 21.8 kg) was charged to the reactor. The contents were heated overnight (~17 h) at 65±5° C., after which the reaction was cooled to 25±5° C. The product was collected by filtration (table top filter, polypropylene cloth), and the product cake was washed with iPrOAc (2×4.36 kg). The product was transferred to Teflon-lined trays and dried in a vacuum oven (270 mBar w/nitrogen bleed) at 55° C. until constant mass was achieved. Desired (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide was obtained as an off-white solid (2.05 kg, 58% yield, 99 wt % purity).

Formation of (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, Form C (Trituration with iPrOAc)

A dry 100 L RB flask was charged with (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (4.70 kg, 9.06 mol) followed by iPrOAc (47 L, 40.9 kg) that was charged through a cartridge filter (1.0 µm inline cartridge). The slurry was agitated at 65±5° C. for approximately 18 hours, after which the slurry was cooled to 25±5° C. The product was collected by filtration (tabletop funnel lined with Whatman filter paper underneath polypropylene filter cloth), and the product cake was washed with iPrOAc (2×8.2 kg). The product was transferred to Teflon-lined trays and dried in a vacuum oven (270 mBar w/nitrogen bleed) at 55° C. until constant mass was achieved. (R)—N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, Form C was obtained as a white solid (4.52 kg, 95% yield). See PCT/US2016/048616 for additional disclosure and characterization of Form C.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:

1. A method for preparing a diastereomerically enriched sulfinamide compound having the formula:

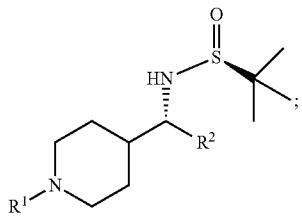

wherein $R^1$ is halo($C_1$-$C_6$)alkyl and $R^2$ is ($C_1$-$C_6$)alkyl, the method comprising
reacting an optically active sulfinylimine compound of the formula

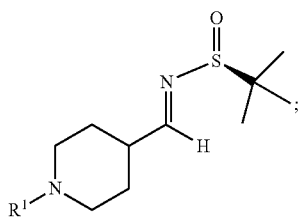

with a nucleophile of the formula $R^2$MgX, wherein X is bromide, iodide, or chloride to form the diastereomerically enriched sulfinamide compound.

2. The method of claim 1, wherein the sulfinamide compound is prepared by reacting the optically active sufinylimine compound with $R^2$MgBr to form the diastereomerically enriched sulfinamide compound.

3. The method of claim 1, wherein the sulfinylimine compound is prepared by reacting an aldehyde compound of the formula:

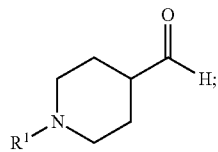

with an optically active compound of the formula

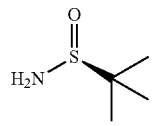

to form the optically active sulfinylimine compound.

4. The method of claim 1, wherein the sufinylimine compound is prepared by reacting an aldehyde compound of the formula:

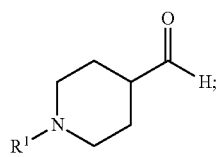

with an optically active compound of the formula

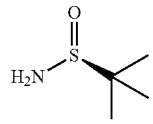

in the presence of an inorganic base to form the optically active sufinylimine compound.

5. The method of claim 1, wherein the optically active sufinylimine compound is prepared by reacting an aldehyde compound of the formula:

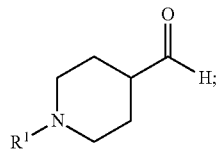

with an optically active compound of the formula

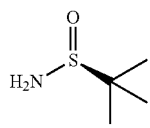

in the presence of Cs$_2$CO$_3$ to form the optically active sufinylimine compound.

6. The method of claim 5, wherein the optically active compound of the formula

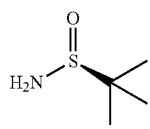

has an enantiomeric excess of >98%.

7. A method for preparing an optically active amine compound having the following formula:

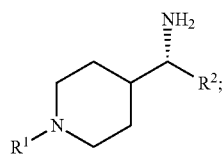

or a salt thereof, wherein R$^1$ is halo(C$_1$-C$_6$)alkyl and R$^2$ is (C$_1$-C$_6$)alkyl,
   the method comprising
      hydrolyzing the sulfinyl group in a diastereomerically enriched sulfinamide compound having the formula:

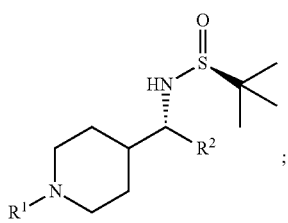

with acid to form the optically active amine compound or the salt thereof.

8. The method of claim 7, wherein the acid is hydrochloric acid.

9. The method of claim 7, further comprising
   a) reacting the optically active amine compound with an optically active organic acid to prepare a diastereomeric salt of the optically active amine compound and the optically active organic acid; and
   b) separating the diastereomeric salt of the optically active amine compound and the optically active organic acid from the diastereomeric salt, if present, of the enantiomer of the optically active amine compound and the optically organic acid.

10. The method of claim 9, wherein diastereomeric salt of the optically active amine compound and the optically active organic acid has the following formula:

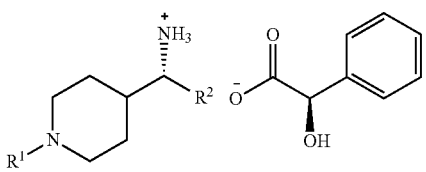

11. A method for preparing an optically active enamine compound of the formula:

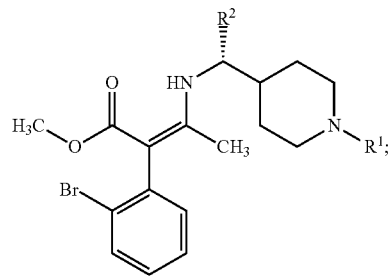

or a salt thereof, wherein R$^1$ is halo(C$_1$-C$_6$)alkyl and R$^2$ is (C$_1$-C$_6$)alkyl,
   the method comprising
      reacting an optically active amine compound or a salt thereof having the formula:

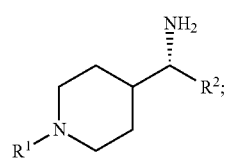

with a di-keto ester compound having the formula:

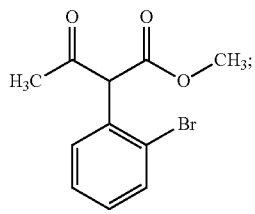

to form the optically active enamine compound or a salt thereof.

12. A method for preparing an optically active indole compound of the formula:

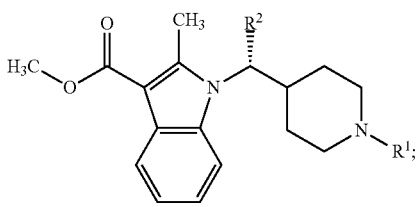

wherein R$^1$ is halo(C$_1$-C$_6$)alkyl and R$^2$ is (C$_1$-C$_6$)alkyl, the method comprising
reacting an optically active enamine salt compound of the formula:

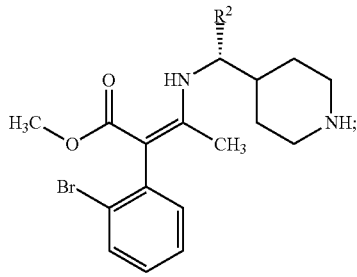

or a salt thereof with base and palladium catalyst to form the optically active indole compound.

13. The method of claim 12, wherein the catalyst is tris(dibenzylideneacetone)dipalladium(0).

14. The method of claim 12, further comprising the step of hydrolyzing the optically active indole compound to form an optically active acid/indole compound having the formula:

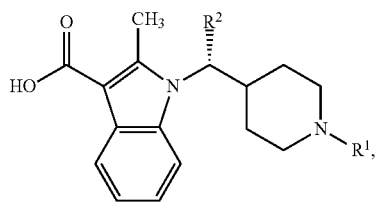

or a salt thereof.

15. A method for preparing an optically active indole pyridine-one having the formula:

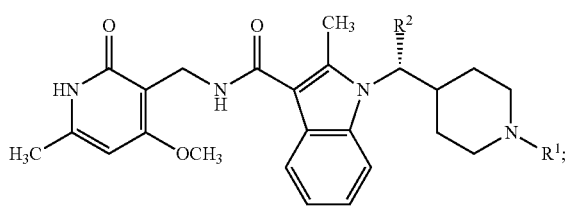

wherein $R^1$ is halo($C_1$-$C_6$)alkyl and $R^2$ is ($C_1$-$C_6$)alkyl, the method comprising
reacting an optically active acid/indole compound of the formula:

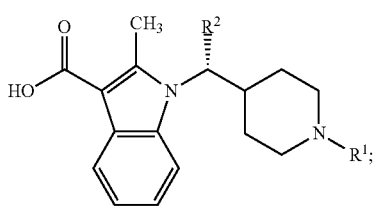

with a free amine compound of the formula:

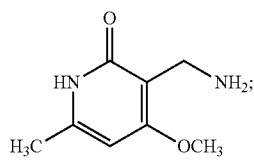

and a carboxylic acid coupling reagent selected from a carbodiimide, a phosphonium reagent, an aminium/uranium-imonium reagent, N-ethoxycarbonyl-2-ethoxy-1,2-dihydroquinoline, 2-propanephosphonic acid anhydride, 4-(4,6-dimethoxy-1,3,5-triazin-2-yl)-4-methylmorpholinium salt, bis-trichloromethylcarbonate, or 1,1'-carbonyldiimidazole to form the indole pyridine-one.

16. The method of claim 1, wherein $R^2$ is —$CH_3$ and $R^1$ is —$CH_2CF_3$.

17. The method of claim 7, wherein $R^2$ is $CH_3$ and $R^1$ is —$CH_2CF_3$.

18. The method of claim 11, wherein $R^2$ is —$CH_3$ and $R^1$ is —$CH_2CF_3$.

19. The method of claim 12, wherein $R^2$ is —$CH_3$ and $R^1$ is —$CH_2CF_3$.

20. The method of claim 15, wherein $R^2$ is —$CH_3$ and $R^1$ is —$CH_2CF_3$.

* * * * *